US008969036B2

(12) United States Patent
Sehdev et al.

(10) Patent No.: US 8,969,036 B2
(45) Date of Patent: Mar. 3, 2015

(54) PROCESS FOR OBTAINING ANTIBODIES

(75) Inventors: Mukesh Sehdev, Slough (GB); Mariangela Spitali, Maidenhead (GB)

(73) Assignee: UCB Pharma S.A., Brussels (BE)

( * ) Notice: Subject to any disclaimer, the term of this patent is extended or adjusted under 35 U.S.C. 154(b) by 737 days.

(21) Appl. No.: 11/791,107

(22) PCT Filed: Nov. 16, 2005

(86) PCT No.: PCT/GB2005/004397
§ 371 (c)(1), (2), (4) Date: May 17, 2007

(87) PCT Pub. No.: WO2006/054063
PCT Pub. Date: May 26, 2006

(65) Prior Publication Data

US 2008/0003644 A1 Jan. 3, 2008

(30) Foreign Application Priority Data

Nov. 19, 2004 (GB) .................................. 0425534.5

(51) Int. Cl.
*C12P 21/06* (2006.01)
*A23J 1/00* (2006.01)
*A61K 39/395* (2006.01)
*C07K 16/00* (2006.01)

(52) U.S. Cl.
CPC ............ *C07K 16/00* (2013.01); *C07K 2317/55* (2013.01)
USPC ....................... 435/69.1; 530/412; 424/130.1

(58) Field of Classification Search
None
See application file for complete search history.

(56) References Cited

U.S. PATENT DOCUMENTS

| | | | | |
|---|---|---|---|---|
| 3,983,008 | A | 9/1976 | Shinozaki et al. | |
| 5,380,826 | A | 1/1995 | Castor et al. | |
| 5,648,237 | A | 7/1997 | Carter | |
| 5,665,866 | A | 9/1997 | Weir et al. | |
| 6,008,023 | A * | 12/1999 | Opper et al. | 435/69.7 |
| 6,120,985 | A * | 9/2000 | Laugharn et al. | 435/1.3 |
| 6,455,287 | B1 * | 9/2002 | Jem | 435/173.7 |

FOREIGN PATENT DOCUMENTS

| | | | | |
|---|---|---|---|---|
| EP | 0 737 747 A2 | | 3/1996 | |
| WO | WO 99/22868 | * | 5/1999 | B01L 11/00 |
| WO | WO2005/019466 | | 3/2005 | |

OTHER PUBLICATIONS

Cui et al., The TyrR Protein of *Escherichia coli*, Analysis by Limited Proteolysis of domain Structure and Ligand-Mediated Conformational Changes, The Journal of Biological Chemistry, 1993, vol. 268, pp. 5040-5047.*
Ribeiro et al., Fast purification of the apo form and of a non-binding heme mutant of recombinant sperm whale myoglobin, Protein Expression and Purification, vol. 28, pp. 202-208.*
Pressure vs. Flow control (last viewed on Aug. 24, 2010).*

(Continued)

*Primary Examiner* — Alexander Kim
(74) *Attorney, Agent, or Firm* — Saliwanchik, Lloyd & Eisenschenk

(57) ABSTRACT

The present invention relates to the manufacture of recombinant antibodies of therapeutic quality. In particular, the invention relates to methods for increasing the yield of functional antibody from large scale fermentations whereby a cultured host cell sample is subjected to a non-lysing treatment.

13 Claims, 5 Drawing Sheets

(56) References Cited

OTHER PUBLICATIONS

Figure 1:
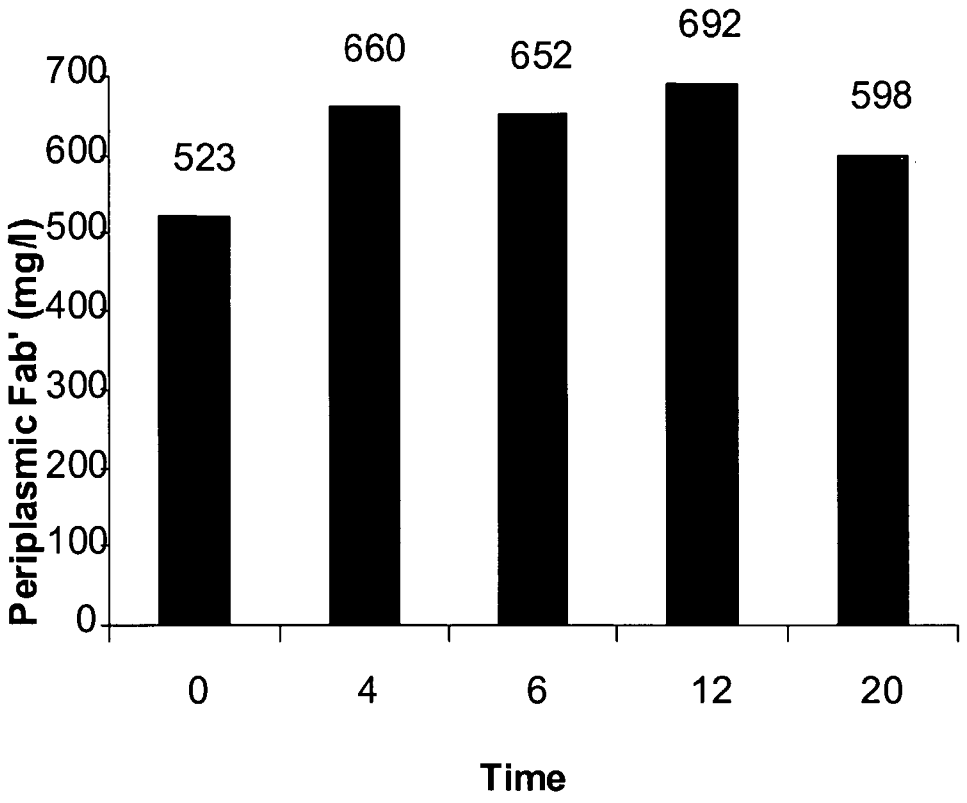

Yoon et al., Effect of Low Culture Temperature on Specific Productivity and Transcription Level of Anti-4-1BB Antibody in Recombinant Chinese Hamster Ovary Cells. Biotechnol. Prog. 2003, vol. 19, pp. 1383-1386.*

Yang et al., A stationary-phase protein of *Escherichia coli* that affects the mode of association between the trp repressor protein and operator-bearing DNA, Proc. Natl. Acad. Sci. USA, (1993), vol. 90, pp. 5796-5800.*

Brownlee et al., Heat treatment of normal human sera reveals antibodies to bactericidal permeability-inducing protein (BPI), Clin Exp Immunol (1999), vol. 117, pp. 183-189.*

Tout, Nancy L., Construction of recombinant antibodies against *Pseudomonas aeruginosa* lipopolysaccharide, Ph.D. thesis 1997.*

Humphreys, David P. et al., "Therapeutic Antibody Production Technologies: Molecules, Applications, Expression and Purification", Current Opinion in Drug Discovery & Development, 2001, vol. 4(2), pp. 172-185.

Johnson, Brian H. et al., "Recombinant Proteins Can Be Isolated from *E. Coli* Cells by Repeated Cycles of Freezing and Thawing", Bio/Technology, vol. 12, Dec. 1994, pp. 1357-1360.

Lemay, Pierre, "The Use of High Pressure for Separation and Production of Bioactive Molecules", Biochimica et Biophysica Acta, vol. 1595, 2002, pp. 357-366.

Casey, J.L., "Purification of Bacterially Expressed Single Chain Fv Antibodies for Clinical Applications Using Metal Chelate Chromatography", Journal of Immunological Methods, vol. 179, 1995, pp. 105-116.

Valdes, Rodolfo et al., "Large-Scale Purification of an Antibody Directed Against Hepatitis B Surface Antigen From Transgenic Tobacco Plants", Biochemical and Biophysical Research Communications, vol. 308, 2003, pp. 94-100.

Mowry, Mark C., "Production and Purification of a Chimeric Monoclonal Antibody Against Botulinum Neurotoxin Serotype A", Protein Expression and Purification, vol. 37, 2004, pp. 399-408.

Popplewell, A. G. et al., "Expression of antibody fragments by periplasmic secretion in *Escherichia coli*", Methods in Molecular Biology, vol. 308, 2005, 15 pages.

Humphreys, D. P. et al., "A plasmid system for optimization of Fab' production in *Escherichia coli*: importance of balance of heavy chain and light chain synthesis", Protein Expression & Purification, vol. 26, 2002, 309-320.

Tsuchido, T. et al., "Destruction of the outer membrane permeability barrier of *Escherichia coli* by heat treatment", Applied and Environmental Microbiology, 50(2), 1985, 298-303.

Middelberg, A., "Process-scale disruption of microorganisms", Biotechnology Advances, 13(3), 1995, 491-551.

Middelberg, A. P.J. et al., "A novel technique for the measurement of disruption in high-pressure homogenization: studies on *E. coli* containing recombinant inclusion bodies", Biotechnology and Bioengineering, vol. 38, 1991, 363-370.

Balasundaram, B. et al., "Significance of location of enzymes on their release during microbial cell disruption", Biotechnology and Bioengineering, 75(5), 2001, 607-614.

Benov, L. et al., "Disrupting *Escherichia coli*: A comparison of methods", Journal of Biochemistry and Molecular Biology, 35(4), 2002, 428-431.

Schnell, J. et al., "Investigations of heat treatment to improve the isolation of intracellular enzymes", Biprocess Engineering, vol. 4, 1989, 129-138.

Schnell, J. et al., "Investigations of heat treatment to improve the isolation of intracellular enzymes", Biprocess Engineering, vol. 5, 1990, 31-38.

Abstract from conference entitled "*Pichia* 2009".

Barer, M.R. "Viable but non-culturable and dormant bacteria: time to resolve and oxymoron and a misnomer," J. Med. Microbiol. 46:629-31 (1997).

Hyka et al., "Combined Use of Fluorescent Dyes and Flow Cytometry to Quantify the Physiological State of *Pichia pastoris* during the Production of Heterologous Proteins in High-Cell-Density Fed-Batch Cultures," Applied and Enviromental Microbiology 76:4486-96 (2010).

Lewis, G. et al., "The application of multi-parameter flow cytometry to the study of recombinant *Escherichia coli* batch fermentation processes," J. Ind. Microbiol. Biotechnol. 31:311-22 (2004).

Sundstrom H et al., "Segregation to non-dividing cells in recombinant *Escherichia coli* fed-batch fermentation processes," Biotechnol. Letts 26:1533-39 (2004).

* cited by examiner (a)

(b)

PROCESS FOR OBTAINING ANTIBODIES

This invention relates to methods for increasing the yields in the production and isolation of functional recombinant antibodies, and in particular therapeutic antibodies. The methods are particularly suitable for the large-scale industrial manufacture of therapeutic antibodies.

Recombinant DNA techniques have rapidly developed and are particularly useful in the production of antibodies, in particular therapeutic antibodies. Systems for the expression of recombinant genes are well known to the person skilled in the field in question. These include expression in mammalian cells, insect cells, fungal cells, bacterial cells and transgenic animals and plants. The choice of expression system is dependent on the features of the encoded protein, for example post-translational modifications. Other considerations include the time and, in particular, the cost involved in the production of the desired quantity of material of the required quality. These latter considerations are particularly important in the production of therapeutic antibodies of the quality required for regulatory approval and in the quantities needed for treatment of large numbers of patients.

The most widely used system for the production of recombinant proteins is based on expression in *Escherichia coli* (*E. coli*). A specific problem encountered with the use of *E. coli* is the difficulty in producing material of the required quality in quantities needed for therapy. In particular, the time and costs involved can be prohibitive. One specific problem of note is the loss incurred in the yield of antibodies during extraction of the antibodies from *E. coli*. A method that partially addresses this latter problem and that permits the production of antibodies acceptable for therapeutic use is described in U.S. Pat. No. 5,655,866. This method involves the use of heat treatment to facilitate the subsequent isolation of functional Fab' fragments of antibodies from non-functional antibodies, the heat treatment being performed at any time during the fermentation or culture, or at any stage during extraction and purification of the antibodies. At elevated temperatures above room temperature, functional antibodies are remarkably stable, whilst many other proteins including host cell proteins and free light and heavy chain species and non-functional fragments of antibodies, form precipitates and/or aggregates which are easily separated from functional antibody during primary purification procedures such as filtration or centrifugation or fluidised bed chromatography. Although, proportionally, the purification costs are a fraction of the total cost of a therapeutic antibody product, the purification cost proportion will increase further as upstream production costs become cheaper. Thus, improvements in recovery and purification of antibodies will drive production costs down further irrespective of the means of production (Humphreys & Glover, Curr. Opin. Drug Discovery & Development, 2001, 4:172-185). Hence, there is a need for methods that introduce time and/or cost savings into therapeutic antibody production and, in particular, in purification, for example by increasing product recovery and/or improving the quality of the product stream.

Low product yield per fermentation or culture is often a particular problem noted at the primary extraction stage; expression of antibody is high within the cells but a high percentage recovery at the primary extraction stage is remarkably difficult to achieve. U.S. Pat. No. 5,665,866 describes enhancement of initial purification yields by the inclusion of a heat treatment step which aids the purification process by removing non-functional antibody.

WO2005019466 (published after the priority date of this application) describes an increase in yield of recombinant proteins by the inclusion of an interruption step after fermentation but prior to downstream processing.

This invention described herein is based on the surprising and unexpected observation that non-lysing treatment in combination with heat treatment, brings an increase in the yield of functional antibody at the primary extraction stage of up to 50%; i.e. the yield of functional antibody is increased above that of heat treatment alone. This enables hugely beneficial savings in time and cost of production of quantities of functional antibodies of therapeutic quality.

Accordingly, provided is a method for the manufacture of recombinant antibody molecules comprising culturing a host cell sample transformed with an expression vector encoding a recombinant antibody molecule and subjecting said sample to non-lysing treatment step.

In a preferred example, the recombinant antibody molecule is at least part of an antibody light chain and at least part of an antibody heavy chain, such that at least some of the expressed light and heavy chain antibody molecules are able to combine to form functional antibody.

In a most preferred embodiment, the method further comprises subjecting the sample to an increase in temperature within the range of 30° C. to 70° C. for a period of up to 24 hours. Thus, the invention also provides a method for increasing the yield of functional antibody molecules isolated from a sample comprising functional antibody molecules and non-functional antibody molecules, which method comprises subjecting the sample to an increase in temperature within the range of 30° C. to 70° C. for a period of up to 24 hours, wherein the sample is subjected to a non-lysing treatment step before being subject to the increase in temperature. An increased yield of functional antibodies isolated or obtained is, therefore, achieved using the methods of the invention.

In particular, the method permits an increase in isolated functional antibody yields at a range of temperatures and treatment conditions, which can be varied as required, and understood by one skilled in the art, to take account of the particular characteristics of the functional antibody being produced and the expression system being used.

As used herein, 'functional antibody' includes antibody molecules that retain the ability to specifically recognise or bind to the antigen against which they were raised (cognate antigen). The production of a functional antibody is shown by the presence of a single band on non-reducing SDS-PAGE corresponding to the expected molecular weight of the antibody, or by direct binding assay using BIACore or other methods known to the person skilled in the art, for example but not limited to, ELISA. Non-functional antibodies include fragments which do not recognise their cognate antigen, and include incorrectly-folded or incorrectly-assembled antibodies, free heavy and light chains, and fragments thereof, including partially degraded fragments of antibodies which do not recognise or bind to their cognate antigen.

In the methods of the invention a sample may be the product of a fermentation (or culture), for example but without limitation, a fermentation comprising bacteria, especially gram-negative bacteria, or yeast, a cell culture, for example but without limitation, a mammalian or insect cell culture. Most preferably, the sample is the product of a fermentation comprising *E. Coli* expressing a recombinant antibody, wherein said antibodies may be functional and non-functional antibodies. If desired, the host cells may be subject to collection from the fermentation medium, e.g. host cells may be collected from the sample by centrifugation, filtration or by concentration. In particular, the methods of the invention are suitable for the large-scale industrial manufacture of antibodies of therapeutic quality.

A further advantage of using non-lysing treatment in the methods of the invention in addition to the surprising increase in yield of functional antibody achieved, is the ease of handling of the sample on a large scale. Lysis causes an increase in viscosity which can cause problems in downstream processing and purification of functional antibody. In particular, lysis of host cells causes release of host cell proteins making purification more expensive and time consuming as more purification steps may be required and/or larger quantities of chromatography materials will be needed to achieve the required purity. Substantial release of host cell DNA increases sample viscosity causing filtration and centrifugation difficulties which is a major cause of protein loss during clarification. A lysed sample (ie. containing host cell proteins and DNA) can also cause blockage of chromatographic materials.

In the invention described herein, non-lysing treatment includes any treatment which does not produce lysis of a substantial proportion of the bacteria, mammalian cell, yeast, insect cell, or other organism used for recombinant antibody expression, e.g. *E. coli*. In a most preferred embodiment, the non-lysing treatment comprises pressure treatment. Alternatively, the non-lysing treatment comprises a pre-conditioning step of agitation or stirring. A "substantial proportion" includes a proportion of 80% or more of the organisms in a fermentation or culture being present in intact form, more preferably more than 85%, even more preferably more than 90%, and most preferably 95% or more being intact.

Lysis can be judged in any way known in the art, including: by viewing under a microscope, fluorescence activated cell sorting (FACS) analysis and assay of total protein versus protein in supernatant and/or in an organism (cell) pellet. In one embodiment, lysis can be judged after non-lysing treatment by comparing the total protein in a sample before and after treatment. If a treatment is causing lysis, the total protein present in the supernatant of the treated sample would increase compared to the total protein present in said untreated sample, for example measured using a Bradford assay. In a preferred embodiment, FACS analysis is performed wherein the sample is labelled with a fluorescent dye followed by non-lysing treatment and FACS analysis. Most preferably, FACS analysis is performed before treatment giving a baseline value for comparison.

Thus, non-lysing treatment can include pre-conditioning by gentle resuspension over a period of time, for example by agitation or stirring, or by manual resuspension such as by pipetting, in, e.g. a buffer. In one embodiment, pre-conditioning is performed for between 1 hour and 24 hours, preferably between 1 hour and 20 hours, more preferably between 2 hours and 18 hours, 4 hours and 16 hours, 6 hours and 16 hours, and most preferably for 12, 14 or 16 hours. Thus, the minimum time for pre-conditioning is 1, 2 or 4 hours and the maximum is 16, 18 or 24 hours. Pre-conditioning can be performed by rotation at 50 to 250 rpm, preferably at 60 rpm to 100 rpm, and most preferably for 14 or 16 hours. During pre-conditioning the cells are maintained at a temperature within the range of 4° C. to 30° C., more preferably between 4° C. to 20° C. and most preferably at room temperature.

In a preferred embodiment, non-lysing treatment comprises subjecting the host cells to increased pressures, for example using a French press or nitrogen decompression. In a specific example, the sample is the product of an *E. coli* fermentation, said *E. coli* expressing a recombinant antibody, which is subjected to pressure treatment in a French press. Pressures may range from 750 psi or thereabouts to 5000 psi or thereabouts. In one embodiment, the pressure treatment is performed at 1000 psi, or 1250 psi, 1500 psi, 1750 psi, 2000 psi, 2250 psi, 2500 psi, 2750 psi, 3000 psi, 3250 psi, 3500 psi, 4000 psi, 4250 psi, 4500 psi or 4750 psi. More preferably, the pressure treatment is performed at between 1000 psi and 3000 psi, and most preferably at 2000 psi. Pressure treatment which is substantially non-lysing (i.e. causing less than 20% lysis) may be determined by simple experimentation depending on the buffer and cell type comprising the sample, and the pressure.

Accordingly, provided is a method for the manufacture of recombinant antibody molecules comprising culturing a host cell sample transformed with an expression vector encoding a recombinant antibody molecule and subjecting said sample to pressure treatment. Also, provided is a method of increasing the yield of functional antibody molecules isolated from a sample, said sample comprising soluble, functional antibody molecules, and non-functional antibody molecules, which method comprises subjecting the sample to an increase in temperature within the range of 30° C. to 70° C. for a period of up to 24 hours, wherein the sample is subjected to a non-lysing treatment step comprising subjecting the sample to increased pressures before being subject to an increase in temperature.

Further provided is a method for the manufacture of recombinant antibody molecules comprising culturing a host cell sample transformed with an expression vector encoding a recombinant antibody molecule and subjecting said sample to preconditioning agitation. The invention also provides a method of increasing the yield of functional antibody molecules isolated from a sample, said sample comprising soluble, functional antibody molecules, and non-functional antibody molecules, which method comprises subjecting the sample to an increase in temperature within the range of 30° C. to 70° C. for a period of up to 24 hours, said method characterised in that the sample is subjected to a non-lysing treatment step comprising pre-conditioning the sample before subjecting the sample to an increase in temperature. Preferably, the non-lysing treatment comprises pre-conditioning agitation for 14 or 16 hours.

Preferably, the host cells are collected from a fermentation or culture, e.g. by centrifugation, and are suspended in a buffered solution using buffered salts such as, but not limited to, Tris, acetate or phosphate. The pH of the solution may, for example, be between pH 2 and pH 10 and will most preferably be between pH 6 and pH 8. In one embodiment, the pH is 6.8 or within 0.1 unit of pH 6.8. A most preferred buffer is Tris buffer, pH 7.4 which may optionally further comprise EDTA, for example but without limitation, 100 mM Tris, pH 7.4 containing 10 mM EDTA. Host cells are preferably suspended in the latter buffer before being subjected to a non-lysing treatment step. The non-lysing treatment may be performed in the growth broth or culture medium as for the fermentation depending on the antibody being purified, for example pre-conditioning in growth broth. Thus, in one example, the increase in yield by pre-conditioning in growth broth varies depending on the antibody being expressed by the host cell. The skilled person can determine experimentally whether pre-conditioning in growth broth is suitable for any particular antibody. Most preferably, the non-lysing treatment is performed in a buffer as described above.

In a most preferred embodiment, the methods of the invention are performed using a fermentation sample of *E. coli* expressing a recombinant antibody. The sample comprises Tris/EDTA buffer between pH 6 and pH 8, preferably pH 7.4, more preferably at pH 6.8, and is subjected to pressure treatment in a French press at 2000 psi.

Most preferably, heat treatment steps are performed within the range of 30° C. to 70° C. The temperature can be selected as desired and may depend on the stability of the antibody for purification. In another embodiment, the temperature is within the range 40° C. to 65° C., or preferably within the range 40° C. to 60° C., more preferably within the range 45° C. to 60° C., even more preferably within the range 50° C. to 60° C. and most preferably at 55° C. to 60° C. Thus, the minimum temperatures are 30° C., 35° C. or 40° C. and the maximum temperatures 60° C., 65° C. or 70° C. The length of heat treatment is preferably between 1 and 24 hours, more preferably between 4 and 18 hours, even more preferably between 6 and 16 hours and most preferably 10 and 14 hours, for example 12 hours. Thus, the minimum time for heat treatment is 1, 2 or 3 hours and the maximum is 20, 22 or 24 hours.

In a particular embodiment, the heat treatment is performed at 50° C. to 60° C. for 12 to 16 hours, and more preferably at 50° C. for 14 hours. One skilled in the art will understand that temperatures and time can be selected as suits the sample in question and the characteristics of the antibody being produced.

Antibody manufacture can additionally comprise primary purification procedures such as filtration and/or centrifugation. Also included is fluidised bed chromatography. Preferred downstream purification procedures include ion exchange chromatography, microfiltration, ultrafiltration, diafiltration, and fixed bed capture and expanded bed capture, and combinations of any of these.

As used herein, 'antibodies' include functionally active fragments, derivatives or analogues and may be, but are not limited to, polyclonal, monoclonal, bi-, tri- or tetra-valent antibodies, humanized or chimeric antibodies, single chain antibodies, such as single chain Fv fragments, Fab fragments, Fab' and Fab'$_2$ fragments, anti-idiotypic (anti-Id) antibodies, and epitope-binding fragments of any of the above. These antibodies and their fragments may be naturally occurring, humanized, chimeric or CDR grafted antibodies and standard molecular biology techniques may be used to modify, add or delete amino acids or domains as desired. Humanized antibodies are antibody molecules from non-human species having one or more complementarity determining regions (CDRs) from the non-human species and a framework region from a human immunoglobulin molecule (see, for example, U.S. Pat. No. 5,585,089). The antibody molecules purified using the methods of the invention can be of any class (e.g. IgG, IgE, IgM, IgD and IgA) or subclass of immunoglobulin molecule.

The methods for creating these antibody molecules are well known in the art (see for example, Shrader et al., WO 92/02551; Ward et al., 1989, Nature, 341:544; Orlandi et al., 1989, Proc. Natl. Acad. Sci. USA, 86:3833; Riechmann et al., 1988, Nature, 322:323; Bird et al, 1988, Science, 242:423; Queen et al., U.S. Pat. No. 5,585,089; Adair, WO91/09967; Mountain and Adair, 1992, Biotechnol. Genet. Eng. Rev, 10:1-142; Verma et al., 1998, Journal of Immunological Methods, 216:165-181).

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic. Bivalent antibodies may be made by methods known in the art (Milstein et al., 1983, Nature 305:537-539; WO 93/08829, Traunecker et al., 1991, EMBO J. 10:3655-3659). Bi-, tri- and tetra-valent antibodies may comprise multiple specificities or may be monospecific (see for example WO 92/22853).

Antibody sequences may also be generated using single lymphocyte antibody methods based on the molecular cloning and expression of immunoglobulin variable region cDNAs generated from single lymphocytes that were selected for the production of specific antibodies such as described by Babcook, J. et al., 1996, Proc. Natl. Acad. Sci. USA 93(15): 7843-7848 and in WO 92/02551. The latter methods rely on the isolation of individual antibody producing cells which are then clonally expanded followed by screening for those clones which are producing an antibody which recognises its cognate antigen, and, if desired, the subsequent identification of the sequence of their variable heavy ($V_H$) and light ($V_L$) chain genes. Alternatively, the cells producing antibody that recognises its cognate antigen may be cultured together followed by screening.

Antibodies prepared using the methods of the invention are most preferably humanised antibodies which may be linked to toxins, drugs, cytotoxic compounds, or polymers or other compounds which prolong the half-life of the antibody when administered to a patient.

Methods for the expression of recombinant proteins are well known in the art. Suitable examples of host cells for the expression of recombinant antibody molecules include bacteria such as gram positive or gram negative bacteria, e.g. *E. coli*, or yeast cells, e.g. *S. cerevisiae*, or mammalian cells, e.g. CHO cells and myeloma or hybridoma cell lines, e.g. NSO cells. Most preferably, in the methods of the invention, a recombinant antibody is produced in bacteria, e.g. *E. coli* (see Verma et al., 1988, J. Immunol. Methods 216:165-181; Simmons et al., 2002, J. Immunol. Methods 263:133-147).

*E. coli* host cells may be naturally occurring *E. coli* strains or mutated strains capable of producing recombinant proteins. Examples of specific host *E. coli* strains include MC4100, TG1, TG2, DHB4, DH5α, DH1, BL21, K12, XL1Blue and JM109. Examples also include modified *E. coli* strains, for example metabolic mutants and protease deficient strains. One preferred *E. coli* host is *E. coli* W3110 (ATCC 27,325) a commonly used host strain for recombinant protein fermentations. The recombinant antibody produced using the methods of the present invention is typically expressed in either the periplasm of the *E. coli* host cell or in the host cell culture supernatant, depending on the nature of the protein and the scale of production. The methods for targeting proteins to these compartments are well known in the art, for a review see Makrides, Microbiological Reviews, 1996, 60, 512-538. Examples of suitable signal sequences to direct proteins to the periplasm of *E. coli* include the *E. coli* PhoA, OmpA, OmpT, LamB and OmpF signal sequences. Proteins may be targeted to the supernatant by relying on the natural secretory pathways or by the induction of limited leakage of the outer membrane to cause protein secretion examples of which are the use of the pelB leader, the protein A leader, the coexpression of bacteriocin release protein, the mitomycin-induced bacteriocin release protein along with the addition of glycine to the culture medium and the coexpression of the kil gene for membrane permeabilization. Most preferably, in the methods of the invention, the recombinant protein is expressed in the periplasm of the host *E. coli*.

Expression of the recombinant protein in the *E. coli* host cells may also be under the control of an inducible system, whereby the expression of the recombinant antibody in *E. coli* is under the control of an inducible promoter. Many inducible promoters suitable for use in *E. coli* are well known in the art and depending on the promoter, expression of the recombinant protein can be induced by varying factors such as temperature or the concentration of a particular substance in the growth medium (Baneyx, Current Opinion in Biotechnology, 1999, 10:411-421; Goldstein and Doi, 1995, Biotechnol. Annu. Rev, 105-128). Examples of inducible promoters include the *E. coli* lac, tac, and trc promoters which are inducible with lactose or the non-hydrolyzable lactose analog, isopropyl-β-D-1-thiogalactopyranoside (IPTG) and the phoA, trp and araBAD promoters which are induced by phosphate, tryptophan and L-arabinose respectively. Expression may be induced by, for example, the addition of an inducer or a change in temperature where induction is temperature dependent. Where induction of recombinant protein expression is achieved by the addition of an inducer to the culture the inducer may be added by any suitable method depending on the fermentation system and the inducer, for example, by single or multiple shot additions or by a gradual addition of inducer through a feed. It will be appreciated that there may be a delay between the addition of the inducer and the actual induction of protein expression for example where the inducer is lactose there may be a delay before induction of protein expression occurs while any pre-existing carbon source is utilized before lactose.

*E. coli* host cell cultures (fermentations) may be cultured in any medium that will support the growth of *E. coli* and expression of the recombinant protein. The medium may be any chemically defined medium, such as those provided in Pirt S. J. (1975) Principles of Microbe and Cell Cultivation, Blackwell Scientific Publications, with modifications where appropriate to control growth rate as described herein. An example of a suitable medium is 'SM6E' as described by Humphreys et al., 2002, Protein Expression and Purification, 26:309-320.

Culturing of the *E. coli* host cells can take place in any suitable container such as a shake flask or a fermenter depending on the scale of production required. Various large scale fermenters are available with a capacity of greater than 1,000 litres up to about 100,000 litres. Preferably, fermenters of 1,000 to 50,000 litres are used, more preferably 1,000 to 10,000 or 12,000 litres. Smaller scale fermenters may also be used with a capacity of between 0.5 and 1,000 litres.

Fermentation of *E. coli* may be performed in any suitable system, for example continuous, batch or fed-batch mode (Thiry & Cingolani, 2002, Trends in Biotechnology, 20:103-105) depending on the protein and the yields required. Batch mode may be used with shot additions of nutrients or inducers where required. Alternatively, a fed-batch culture may be used and the cultures grown in batch mode pre-induction at the maximum specific growth rate that can be sustained using the nutrients initially present in the fermenter and one or more nutrient feed regimes used to control the growth rate until fermentation is complete. Fed-batch mode may also be used pre-induction to control the metabolism of the *E. coli* host cells and to allow higher cell densities to be reached (Lee, 1996, Tibtech, 14:98-105).

Preferred features of each embodiment of the invention are as for each of the other embodiments *mutatis mutandis*. All publications, including but not limited to patents and patent applications cited in this specification are herein incorporated by reference as if each individual publication were specifically and individually indicated to be incorporated by reference herein as though fully set forth.

The invention will now be described with reference to the following examples, which are merely illustrative and should not in any way be construed as limiting the scope of the present invention.

FIG. 1 is a histogram showing the effect of pre-conditioning treatment (agitation) on the yield of functional antibody A. Time of pre-conditioning is shown in hours. Numbers above each bar indicate functional antibody A yield in mg/litre clarified resuspension.

Figure 2:
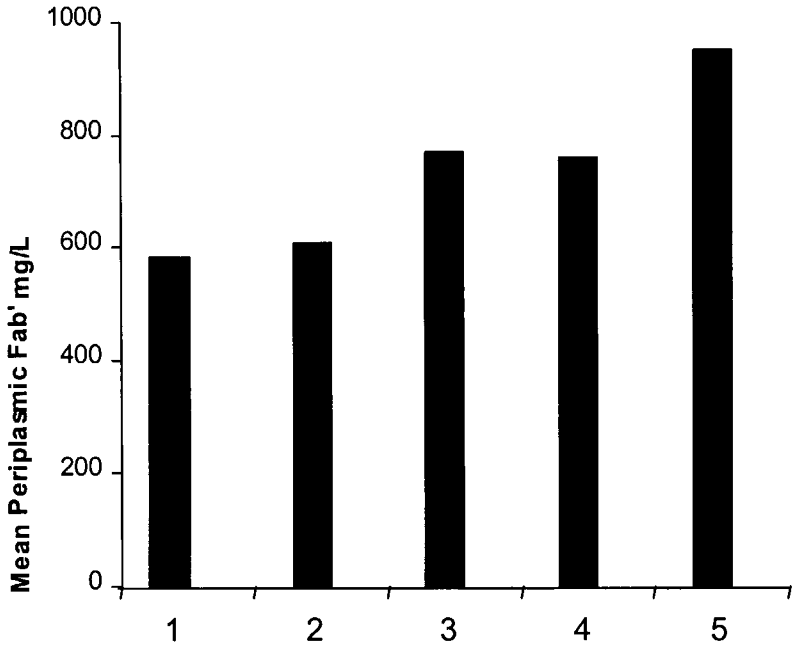

FIG. 2 is a histogram showing the effect of pressure treatment on the yield of functional antibody A: Bar 1 is a control with no pressure treatment; bars 2, 3, 4 and 5 represent treatment at 500 psi, 1000 psi, 2000 psi and 4000 psi, respectively.

Figure 3:
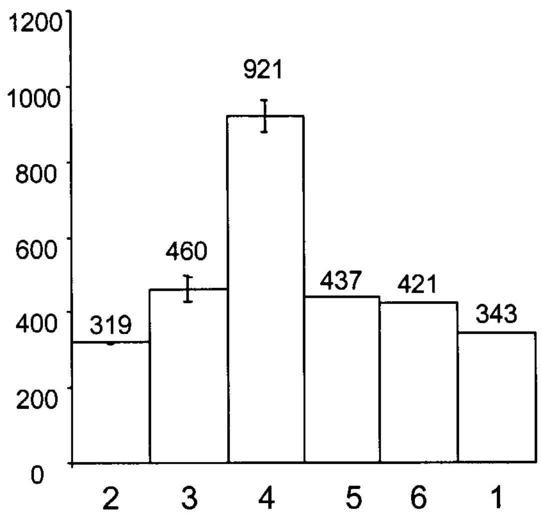
Figure 3:
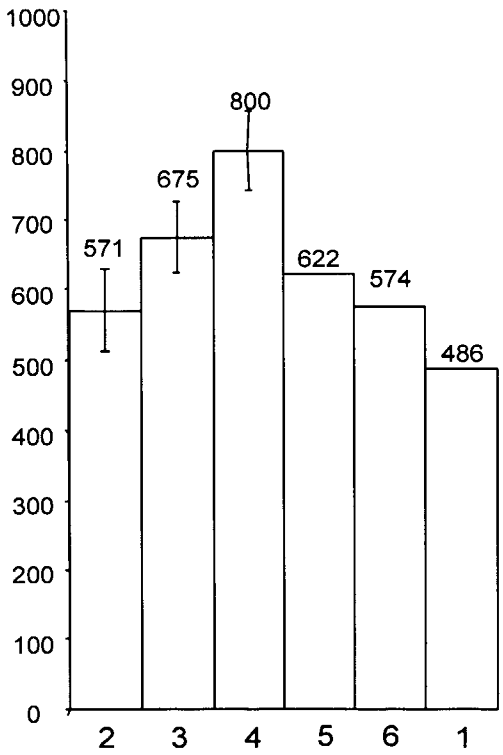

FIGS. 3*a*) and *b*) are histograms showing the effect of pressure treatment and pre-conditioning on the yield of functional antibody B at 60° C. (Panel 3a) and 30° C. (Panel 3b): In each case Bar 1 is a control with no non-lysing treatment; bars 2, 3 and 4 represent treatment at 1000 psi, 2000 psi and 4000 psi, respectively. Bars 5 and 6 represent 24 hours of pre-conditioning treatment in Tris/EDTA at room temperature (bar 5) or 4° C. (bar 6). Numbers above each bar indicate functional antibody B yield in mg/litre clarified resuspension. All experiments were performed in duplicate.

Figure 4A:
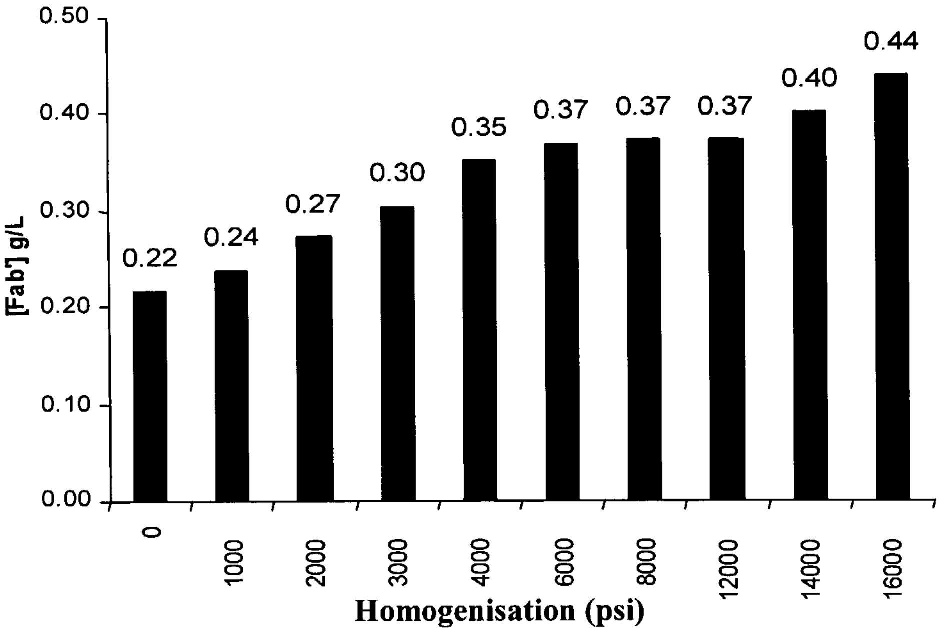

FIGS. 4*a*) and *b*) are histograms with panel a) showing the effect of pressure treatment on the yield of functional antibody C following extraction at 60° C. expressed as grams Fab' per litre and panel b) showing the total protein present in the clarified extract after the heat treatment. In panel a), numbers above each bar indicate functional antibody C yield in g/litre clarified resuspension.

Figure 5:
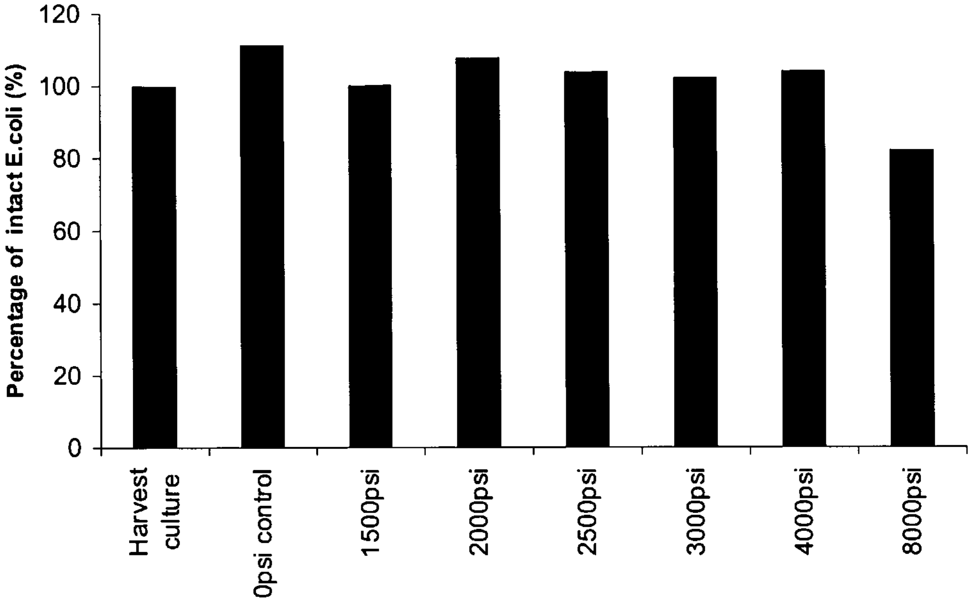

FIG. 5 is a histogram showing the effect of pressure treatment on cell lysis using FACS analysis of *E. coli* in the presence of propidium iodide.

EXAMPLE 1

Effect of Non-Lysing Treatment (Pre-Conditioning)

(a) Antibody A (a Fab') was expressed in *E. coli* W3110 cells using the vector pTT0D with DNA encoding antibody A inserted. Fermentation (in DD53) was performed at 25° C. until $OD_{600}$ was 111.6 and ready for harvest. Fifty ml harvest culture aliquots at room temperature were centrifuged and the cell pellets resuspended in 5 ml of culture supernatant plus 29 ml $H_2O$ and 5 ml of 1 M Tris, pH 7.4 containing 100 mM EDTA. Resuspended cell pellets were subjected to pre-conditioning agitation at 60 rpm for times as indicated in FIG. 1. Following pre-conditioning the resuspended cell pellets were subjected to heat treatment at 50° C. with agitation at 170 rpm for 14 hours. Post heat treatment, the resuspended cell pellets were clarified by centrifugation at 4200 rpm in a Beckman J. 6 centrifuge for 30 mins at 4° C. Supernatant containing functional antibody A was assayed for Fab' using Protein G HPLC analysis in 20 mM phosphate buffer. Antibody A was eluted using a pH gradient from pH 7.4 on injection, reducing to pH 2.5. Functional antibody yields were calculated by comparison with a standard Fab' concentration.

An increase in yield of functional antibody can be seen at all times of pre-conditioning agitation compared to no pre-conditioning agitation (FIG. 1). An increase in yield of functional antibody A of around 30% was achieved at all time points by the use of this non-lysing treatment.

(b) Antibody B (a Fab') was expressed in *E. coli* W3110 cells using the vector pTT0D with DNA encoding antibody B inserted as described above. Fifty ml harvest culture aliquots at room temperature were centrifuged and the cell pellets resuspended in 5 ml of culture supernatant plus 29 ml H₂O and 5 ml of 1 M Tris, pH 7.4 containing 1000 mM EDTA before being subjected to pre-conditioning agitation at 60 rpm at room temperature or 4° C. for 24 hours (see FIGS. 3a and b). Heat treatment and clarification was performed as described above but at the temperatures indicated in the legend to FIGS. 3a and 3b.

An increase in yield of functional antibody can be seen at room temperature and 4° C. for those resuspensions in Tris/EDTA.

EXAMPLE 2

Effect of Non-Lysing Treatment (Pressure)

(a) Antibody A was expressed in *E. coli* as described in Example 1. Resuspended cell pellets were prepared in culture supernatant, H₂O and Tris/EDTA, as in Example 1, before being subjected to pressure treatment at various pressures using a French press. Heat treatment was performed and functional antibody yields calculated as described in Example 1.

An increase in yield of functional antibody can be seen at all pressures except 500 psi compared to no pressure (FIG. 2). An increase in yield of functional antibody A was achieved by the use of this non-lysing treatment, particularly at 1000 psi and 2000 psi. At 4000 psi some cell lysis was apparent but this was not substantial (i.e. less than 20%).

(b) Antibody B (a Fab') was expressed in *E. coli* W3110 cells using the vector pTT0D with DNA encoding antibody B inserted. Fermentation was performed and resuspended cell pellets were prepared in culture supernatant, H₂O and Tris/EDTA, as described in Example 1 before being subjected to pressure treatment at various pressures using a French press. Heat treatment was performed at (i) 30° C. (FIG. 3a) or (ii) 60° C. (FIG. 3b) with agitation at 170 rpm for 14 hours. Post heat treatment, the cell resuspension was clarified by centrifugation and functional antibody yields calculated as described in Example 1.

An increase in yield of functional antibody B was achieved by the use of this non-lysing treatment, particularly at 1000 psi and 2000 psi but not at 500 psi (FIGS. 3a & 3b). At 4000 psi some cell lysis was apparent but this was not substantial.

(c) Antibody C (a Fab') was expressed in *E. coli* W3110 cells using the vector pTT0D with DNA encoding antibody C inserted. Fermentation was performed and resuspended cell pellets were prepared in culture supernatant, H₂O and Tris/EDTA, as described in Example 1 before being subjected to pressure treatment at various pressures using a French press. Heat treatment was performed at 60° C. (FIG. 4) with agitation at 170 rpm for 14 hours. Post heat treatment, the cell resuspension was clarified by centrifugation and functional antibody yields calculated as described in Example 1.

Figure 4B:
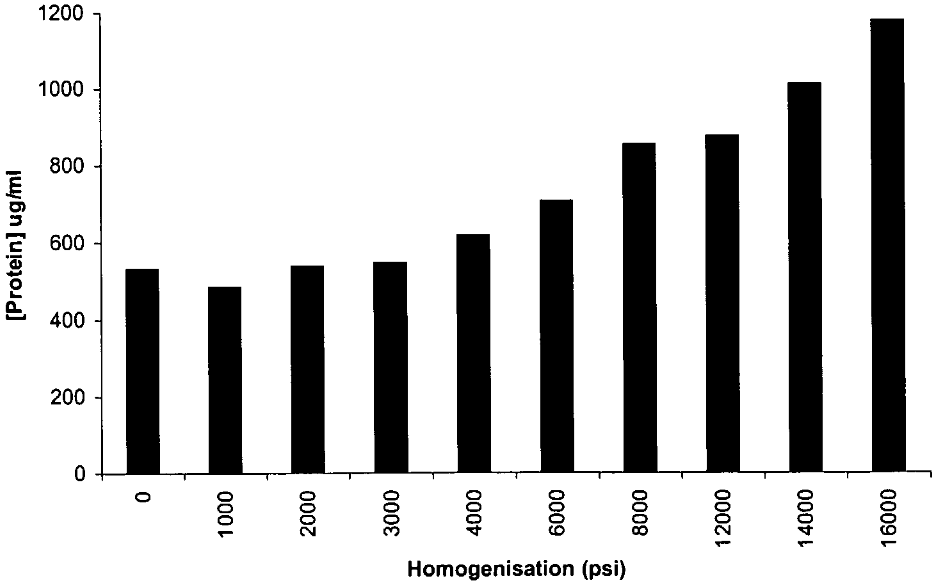

An increase in yield of functional antibody can be seen at mild pressures of between 1000 psi and 4000 psi compared to no pressure (FIG. 4a) while very little increase in total protein (Fab' plus any host cell proteins), as measured by Bradford assay, can be seen (FIG. 4b). This result is confirmed by SDS-PAGE analysis of the clarified extract (not shown). These results indicate that no substantial lysis of host cells occurred at pressures of between 1000 to 4000 psi. Thus, an increase in yield of functional antibody C post 60° C. heat treatment was achieved by the use of this non-lysing treatment.

(d) Antibody D (a Fab') was expressed in *E. coli* W3110 cells using the vector pTT0D with DNA encoding antibody D inserted. Fermentation was performed and harvested by centrifugation. The resuspended cell slurry was prepared in extraction buffer (100 mM Tris/10 mM EDTA, pH 7.4) to original volume and was subjected to pressure treatment at various pressures through a MG homogeniser (single pass). Heat treatment was performed at 60° C. with agitation at 170 rpm for 14 hours. Post heat treatment, the cell resuspension was clarified by centrifugation and functional antibody yields calculated as described in Example 1.

An increase in yield of functional antibody can be seen at mild pressures of between 1000 psi and 4000 psi compared to no pressure while very little increase in total protein (Fab' plus any host cell proteins), as measured by Bradford assay, can be seen (Table 1).

TABLE 1

Increase in Antibody Yield with Non-Lysing Treatment

| Pressure | Concentration Fab' (g/l) | Total protein (g/l) |
|---|---|---|
| 0 psi | 0.685 | 1.46 |
| 2000 psi | 0.794 | 1.26 |
| 3000 psi | 0.878 | 1.46 |
| 4000 psi | 0.896 | 1.50 |

EXAMPLE 3

Measurement of Cell Lysis Using FACS Analysis

Antibody A (a Fab') was expressed in *E. coli* W3110 cells using the vector pTT0D with DNA encoding antibody A inserted. The cell slurry was resuspended in tris/EDTA extraction buffer to original volume, as described in Example 1, and passed through a MG homogeniser (single pass) at various pressures (see FIG. 5).

The feed streams from the homogeniser were collected and diluted to an $OD_{600}$ of 0.2 in phosphate buffered saline. Propidium iodide (200 µg/ml), a fluorescent dye, was added (2 µl) to each sample (500 µl). Propidium iodide binds to DNA but cannot cross an intact cytoplasmic membrane. Each reaction was assessed using a Becton Dickinson FACSCalibur to determine lysed and non-lysed cells. Harvest culture and 0 psi controls were included and indicate total intact cells before pressure treatment. The data shown in FIG. 5 indicate that pressure treatment up to and including 4000 psi results in no cell lysis compared to the harvest culture and 0 psi control. In contrast, raising the pressure to 8000 psi results in an increase in propidium iodide uptake and, thus, some cell lysis.

The invention claimed is:
1. A method for the manufacture of a recombinant antibody or an epitope binding fragment thereof, the method comprising:
   (a) culturing a host cell sample transformed with an expression vector encoding a recombinant antibody,
   (b) subjecting said host cell sample to a pressure treatment at a pressure between 750 psi and 5000 psi, such that said pressure treated host cell sample is less than 20% lysed, and then
   (c) subjecting said sample treated with said pressure to a temperature within the range of 30° C. to 70° C. for a period of 1-24 hours.
2. The method according to claim 1, wherein the pressure treatment is performed between 1000 psi and 4000 psi.
3. The method according to claim 2, wherein the pressure treatment is performed at 2000 psi.

4. The method according to claim 1 which additionally comprises at least one purification step, said purification step being performed after the method steps (a)-(c) of claim 1.

5. The method according to claim 1, wherein the recombinant antibody is a monoclonal, humanised or chimeric antibody.

6. The method according to claim 1, wherein the antibody is a single chain Fv, Fab, Fab' or $F(ab')_2$.

7. The method according to claim 1, wherein during the pressure treatment in step (b) the host cell sample is suspended in a buffered solution having a pH between 6 and 8.

8. The method according to claim 7, wherein the pH is 6.8 or within 0.1 unit of pH 6.8.

9. The method according to claim 7, wherein the buffered solution has the pH of 7.4.

10. The method according to claim 9, wherein the buffered solution comprises 100mM Tris and 10mM EDTA.

11. The method according to claim 9, wherein the buffer solution consists of 100mM Tris and 10 mM EDTA.

12. The method according to claim 1, wherein the pressure treated host cell sample is less than 10% lysed.

13. The method according to claim 1, wherein the pressure treated host cell sample is less than 5% lysed.

* * * * *